United States Patent [19]

Janata

[11] 4,198,851
[45] Apr. 22, 1980

[54] METHOD AND STRUCTURE FOR DETECTING THE CONCENTRATION OF OXYGEN IN A SUBSTANCE

[75] Inventor: Jiri Janata, Salt Lake City, Utah

[73] Assignee: University of Utah, Salt Lake City, Utah

[21] Appl. No.: 908,524

[22] Filed: May 22, 1978

[51] Int. Cl.² ............................................. G01N 31/06
[52] U.S. Cl. ....................................... 73/23; 73/27 R; 422/98
[58] Field of Search .................. 73/23, 27 R; 357/25; 324/71 SN; 422/98

[56] References Cited

U.S. PATENT DOCUMENTS

| | | | |
|---|---|---|---|
| 3,831,432 | 8/1974 | Cox | 73/27 R |
| 3,999,122 | 12/1976 | Winstel et al. | 324/71 SN |
| 4,020,830 | 5/1977 | Johnson et al. | 357/25 |

OTHER PUBLICATIONS

"Chemically Sensitive Field-Effect Transistors", Biomedical Engineering Jul. 1976 (241-245).
"Hemoglobin Studies, II. A Synthetic Material with Hemoglobin-Like Property," J.A. Chem. Soc vol. 80, 6/20/58 pp. 3168-3169, Wang.

Primary Examiner—Anthony V. Ciarlante
Attorney, Agent, or Firm—Thorpe, North & Gold

[57] ABSTRACT

A field-effect transistor structure is utilized for detecting the concentration of oxygen in a substance to which the structure is exposed. The structure includes a semiconductor substrate material having one doping polarity, a pair of spaced apart diffusion regions located at the surface of the substrate material and having a doping polarity opposite that of the substrate material, electrical insulator material overlying the diffusion regions and the surface of the substrate material lying therebetween, a membrane composed of an oxygen binding material overlying at least a portion of the insulator material, and a reference electrode connected in circuit with the diffusion regions and the substrate material. When the membrane is exposed to a substance containing oxygen, the work function of the membrane is changed and this change affects the conductivity between the two diffusion regions which may be measured to yield an indication of the concentration of oxygen in the substance.

3 Claims, 2 Drawing Figures

METHOD AND STRUCTURE FOR DETECTING THE CONCENTRATION OF OXYGEN IN A SUBSTANCE

BACKGROUND OF THE INVENTION

This invention relates to a solid state device and method for measuring the concentration of oxygen in a substance to which the device is exposed.

The need for measuring the concentration of oxygen in biological fluids has led to the development of several oxygen sensing devices including the so-called Clark oxygen electrode. This device includes an electrode assembly in which is contained a metal cathode, an electrolyte solution surrounding the metal cathode, a reference anode also disposed in the electrolyte, and an oxygen-permeable membrane stretched across an opening in the electrode assembly to contain the electrolyte and yet to allow diffusion therethrough of oxygen to which the electrode assembly is exposed. Such oxygen also then diffuses through the electrolyte to the cathode where, as a result of reduction of the oxygen, a current is produced, with this current being proportional to the extent of oxygen reduction. This type of device relies upon the mass transport of oxygen to the cathode and because of this, the device is sensitive to any factor which would affect mass transport such as temperature, amount of electrolyte through which the oxygen must diffuse, external pressure, accumulation of products of the electrochemical reactions, etc. In other words, the Clark electrode is a nonequilibrium device so that with the passage of time, the readout of the device may change and possibly introduce error. Also, the response time is fairly long because of the distance over which the oxygen molecules must diffuse and thus the time needed for the oxygen to diffuse.

There are a number of other oxygen sensing devices which can only operate at high temperatures—generally above 200° C.—because of the materials used in the devices. These devices (typically referred to as "high temperature oxygen sensors"), of course, are limited to high temperature applications.

In U.S. Pat. No. 4,020,830 issued May 3, 1977, a chemical sensitive field-effect transistor transducer is disclosed wherein such transducer has the capability of selectively detecting and measuring chemical properties of substances. This type of transducer eliminates the need for an electrolyte which, of course, simplifies fabrication of the device. This device utilizes a field-effect transistor arrangement for simply and efficiently measuring various chemical properties of substances. Specific embodiments for sensing oxygen were not discussed in the patent, however.

In view of this prior art, it would appear desirable to provide a solid state structure for measuring the concentration of oxygen in a substance, where such structure would not be influenced by mass transport problems or temperature limitations.

SUMMARY OF THE INVENTION

It is an object of the present invention to provide a new and improved solid-state device for measuring oxygen concentration of a substance.

It is another object of the invention to provide such a device which does not rely upon steady state mass transport of oxygen in order to obtain an accurate measure of the oxygen concentration.

It is still another object of the invention to provide such a device which has a fairly fast response time for yielding a reading when exposed to an oxygen containing substance.

It is an additional object of the invention to provide such a device which can operate at room temperature.

It is a further object of the invention to provide a simple, compact and reliable method and structure for detecting the concentration of oxygen in a substance.

The above and other objects of the invention are realized in a solid state sensor which includes a semiconductor substrate having a first doping polarity, a pair of spaced apart diffusion regions located at the surface of the substrate material and having a second doping polarity opposite that of the substrate material, an electrical insulator material overlying at least a portion of the diffusion regions and the surface of the substrate material lying therebetween, a membrane composed of an oxygen binding material overlying at least a portion of the insulator material, and a reference electrode connected in circuit with the diffusion regions through a potential source. The conductivity between the diffusion regions varies as the work function of the membrane varies. The work function of the membrane, in turn, varies according to the concentration of oxygen to which the membrane is exposed. In this manner, the conductivity between the diffusion regions serves as a measure of the concentration of oxygen.

Such a device is a so-called equilibrium device and does not rely upon steady state mass transport of oxygen. Also, the device can operate at room temperature and has a rapid response time since the reaction of oxygen with the oxygen binding material occurs quite rapidly.

BRIEF DESCRIPTION OF THE DRAWINGS

The above and other objects, features and advantages of the present invention will become apparent from a consideration of the following detailed description presented in connection with the accompanying drawings in which.

DETAILED DESCRIPTION

Figure 1:
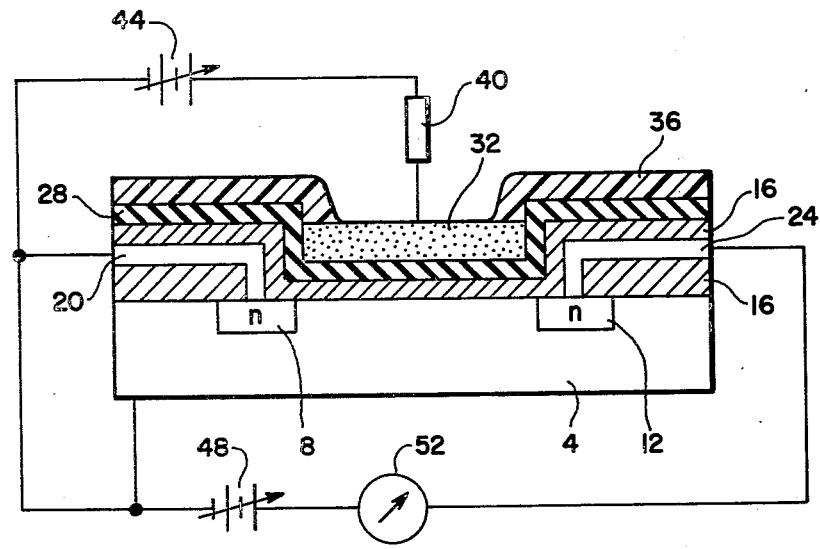
FIG. 1 is a cross-sectional view of a solid state oxygen sensor made in accordance with the principles of the present invention.

The solid state sensor of FIG. 1 is constructed basically of a field-effect transistor (FET) and includes a p-type silicon substrate 4, and two n-type regions 8 and 12 diffused into the surface of the substrate 4 to a depth, for example, of from one to two microns and spaced about twenty microns apart. In a typical metal oxide semi-conductor FET, the diffusion region 8 is referred to as the source and the diffusion region 12 is referred to as the drain. Also included in the sensor of FIG. 1 is a thin layer of electrical insulator material 16, such as silicon dioxide, deposited over the substrate 4 and portions of the diffusion regions 8 and 12. Conductive layers 20 and 24, such as aluminum, n-type silicon, etc., are deposited respectively onto the source diffusion region 8 and the drain diffusion region 12 to provide electrical contact therewith. A second thin layer of electrical insulator material 28, such as silicon nitride, is deposited over the insulator layer 16. Silicon dioxide is included to ensure stable operation of the FET.

Silicon nitride is included because it provides protection against hydration if, for example, the sensor is used in aqueous solutions.

Overlying what is known as the gate region of the FET portion of the sensor of FIG. 1 is a membrane 32 composed of a reversible oxygen binding material. Illustratively, such membrane could be a substituted metallo porphyrin imbedded or included in a polymeric matrix. Specifically, the material could include a 1-(2-phenyl-ethyl)-imidazolecarbonmonoxyheme diethyl ester imbedded in an amorphous mixture of polystyrene and 1-(2-phenyl-ethyl)-imidazole. (This material is described in J. A. Chem. Soc, Vol. 80, June 20, 1958, pp. 3168-3169.) Such a membrane reversibly binds molecular oxygen to which the membrane is exposed, and such activity changes the work function of the membrane to thereby affect the conductivity of the FET of FIG. 1. This will be discussed in more detail later.

The device of FIG. 1, except for a portion of the membrane 32, is covered with some type of material 36 which would generally be impervious to substances to which the device would be exposed. The material 36 could, for example, be comprised of a polymerized epoxy resin. This material would cover all parts of the device including the electrical leads, support structure, etc., which might be immersed in a solution or placed in contact with an oxygen containing substance. Preferably the material would be biocompatible, that is, it would not adversely interact with a solution or human tissue to which the device were exposed.

The circuitry of the device of FIG. 1 includes a reference electrode 40 composed, for example, of a silver core and silver chloride exterior layer. The reference electrode is provided to establish a reference voltage for operation of the device. The reference electrode 40 is coupled to the positive side of a voltage source 44 which develops the desired reference voltage. A voltage source 48 is also provided between the source electrode 20 and drain electrode 24 to establish a potential difference sufficient to cause current flow in the area between the diffusion regions 8 and 12 (this area is known as the conducting channel). An ammeter 52 is coupled between the voltage source 58 and the drain electrode 24 to measure the drain current. The negative terminals of the voltage sources 44 and 48 are coupled together, and to the source electrode 20 and the substrate 4.

When the device of FIG. 1 (the membrane 32 and reference electrode 40) is exposed to a substance containing oxygen, oxygen molecules in the substance combine with the membrane 32 so that the work function of the membrane is changed. "Work function" may generally be defined as the energy required to remove an electron from the membrane to a location spaced an infinite distance from the membrane. The change in the work function of the membrane affects the drain current of the FET in accordance with the following formula:

$$I_D = a[(V_G - V_T)V_D - V_D^2/2],$$

where:
$a = [CW\mu]/L$,
$V_G$ is the gate voltage,
$V_D$ is the drain voltage,
C is the capacitance between the membrane and the semi-conductor substrate 4,
W is the width of the conducting channel between the diffusion regions 8 and 12,
L is the length of the conducting channel,
$\mu$ is the mobility of electrons in the membrane,
$V_T = \nabla\phi_{ms} - Q_{BB}/C + 2\phi_F - Q_{SS}/C$,
$\nabla\phi_{ms}$ is the difference in the work functions of the semi-conductor substrate 4 and the membrane 32,
$Q_{BB}$ is the depletion charge density of the semi-conductor substrate 4,
$Q_{SS}$ is the trapped charged density between insulator layers 16 and 28, and
$\phi_F$ is the Fermi level of the semi-conductor substrate 4.

This formula shows that the drain current, and thus the conductivity between the diffusion regions 8 and 12, is dependent upon the work function of the membrane 32 which changes by an amount proportional to the amount of oxygen which combines with the membrane 32 and becomes bound therewith, and thus to the concentration of oxygen to which the membrane 32 is exposed. In effect, the conductance of the channel formed between the two diffusion regions 8 and 12 is dependent upon the magnitude of the charge at the interface between the substrate 4 and the insulator 16 which, in turn, is dependent upon the work function of the membrane 32.

Figure 2:
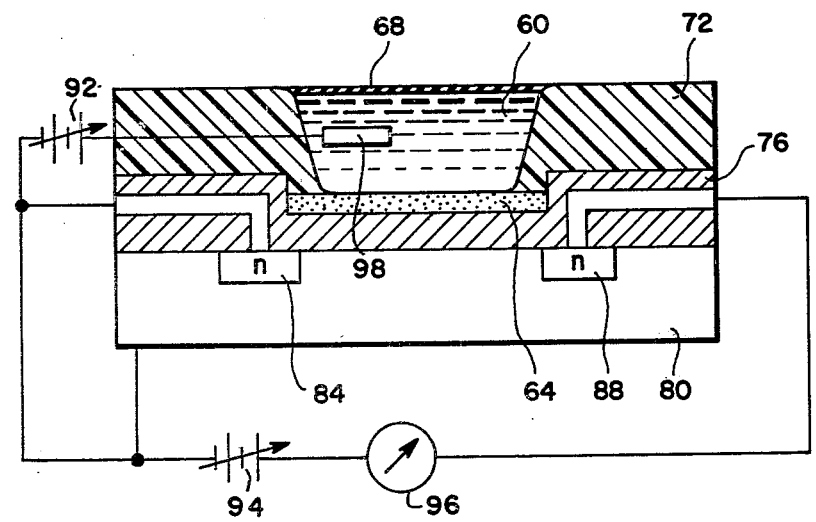
FIG. 2 is a cross-sectional view of an alternative embodiment of an oxygen sensor especially adapted for measurement of oxygen concentration in gasious samples and in electrically non-conducting liquids.

FIG. 2 shows an alternative embodiment of a device which is especially suitable for measuring the oxygen concentration of gases or electrically non-conducting liquids. This embodiment is similar to that of FIG. 1 except that an electrolyte solution 60, such as a saturated solution of potassium chloride, is disposed over the oxygen binding membrane 64 and contained in such position by an oxygen permeable membrane 68, such as silastic teflon having a thickness of about 1 mil. As with FIG. 1, a solution impervious material 72 covers the device and a layer of insulator material 76 is deposited over a semi-conductor substrate 80 having a pair of spaced-apart diffusion regions 84 (source) and 88 (drain). The other parts of the device are the same as that of FIG. 1 and include voltage sources 92 and 94, an ammeter 96, and a reference electrode 98.

Provision of the electrolyte solution assures good electrical contact between the reference electrode and the FET portion of the device and, for this reason, enables measurement of oxygen in non-conducting fluids.

The following process may be followed in preparing the membranes 32 and 64 on the illustrated devices:

1. A mixture of 100 mg of hemin dimethyl ester and 253 mg of phenylethyl-imidazole (i.e., 10 times molar excess) is dissolved in 3 ml of toluene.

2. Two ml of aqueous $Na_2S_2O_4 + KOH$ is added under carbon monoxide atmosphere, and the mixture is shaken.

3. Separate the bright red toluene layer from the aqueous layer by centrifuging and store in a bottle with septum under carbon monoxide atmosphere (solution A).

4. Dissolve 2.27 g of polystyrene in 3 ml of tolurene and saturate with carbon monoxide (solution B).

5. Mix solutions A and B under carbon monoxide atmosphere to obtain polystyrene/phenyl-ethyl-imidazole ratio of between ½ to 9/10 (solution C).

6. Using a syringe, cast solution C onto insulator material overlying the gate region of the FET, under nitrogen atmosphere.

7. Heat the device under carbon monoxide atmosphere to about 80° C. for about five hours.

8. Allow to cool for about 24 hours under a nitrogen atmosphere.

A membrane prepared as indicated enables reversible binding of oxygen molecules therein so that once the device has been used to detect oxygen concentration, the binding of the oxygen can be reversed and the oxygen removed from the membrane. This is done simply by exposing the membrane to an oxygen-free atmosphere such as nitrogen.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A solid state sensor for detecting the concentration of oxygen in a substance to which the sensor is exposed, said sensor comprising
   a semi-conductor substrate having a first doping polarity,
   a pair of spaced-apart diffusion regions located at the surface of said substrate material and having a second doping polarity opposite that of the substrate material,
   an electrical insulator material overlying at least a portion of said diffusion regions and the surface of the substrate material lying between the diffusion regions,
   a membrane overlying at least a portion of said insulator material, said membrane comprising a metallo porphyrin included in a polymeric matrix whose work function changes with a change in the concentration of molecular oxygen bound to the membrane, and
   a reference electrode connected in circuit with said diffusion regions through a potential source,
   the conductivity between said diffusion regions thereby being a measure of the work function change of said membrane which, in turn, is a measure of the concentration of oxygen to which the membrane is exposed.

2. A sensor as in claim 1 wherein said substituted metallo porphyrin comprises a 1-(2-phenyl-ethyl)-imidazolecarbonmonoxyheme diethyl ester imbedded in an amorphous mixture of polystyrene and 1-(2-phenyl-ethyl)-imidazole.

3. A method of detecting the concentration of oxygen in a substance comprising
   providing a field-effect transistor transducer which includes
   a semi-conductor substrate having a first doping polarity,
   a pair of spaced-apart diffusion regions located at the surface of said substrate material and having a second doping polarity opposite that of the substrate material,
   an electrical insulator material overlying at least a portion of said diffusion regions and the surface of the substrate material lying between the diffusion regions,
   a membrane overlying at least a portion of said insulator material, said membrane comprising a substituted metallo porphyrin included in a polymeric matrix, and
   a reference electrode connected in circuit with said diffusion regions through a potential source,
   exposing said membrane and reference electrode to a substance containing oxygen, and
   measuring the conductivity between the two diffusion regions of the transducer.

* * * * *